United States Patent [19]
Li et al.

[11] Patent Number: 5,859,200
[45] Date of Patent: Jan. 12, 1999

[54] HUMAN AMINE TRANSPORTER

[75] Inventors: Yi Li, Gaithersburg, Md.; Liang Cao, Hong Kong, Hong Kong; Craig A. Rosen, Laytonsville, Md.

[73] Assignee: Human Genome Sciences, Inc., Rockville, Md.

[21] Appl. No.: 894,840

[22] PCT Filed: Mar. 1, 1995

[86] PCT No.: PCT/US95/02645

§ 371 Date: Jan. 30, 1998

§ 102(e) Date: Jan. 30, 1998

[87] PCT Pub. No.: WO96/27009

PCT Pub. Date: Sep. 6, 1996

[51] Int. Cl.$^6$ .................................................. C07K 14/47
[52] U.S. Cl. ............................................................. 530/350
[58] Field of Search .............................................. 530/350

[56] References Cited

PUBLICATIONS

Erickson, J. D., (1992) Proc. Natl. Acad. Sci., USA 89, 10993–10997.
Peter, D., (1993) Genomics 18, 720–723.
Krejci, E., et al. (1993) FEBS Lett. 335(1), 27–32.
Surratt, C.K., et al. (1993) FEBS Lett. 318(3), 325–330.
Liu, Y., et al. (1992) Cell 70, 539–551.
Liu, L, et. al. (1994) Mol. Brain Res. 25, 90–96.
Wall, S.C., et al. (1995) Mol. Pharmacol. 47, 544–550.
GenBank Accession No. D28289, Minobe, Y. and Sasaki, T., "RICR0716A Rice root Oryza sativa cDNA, mRNA sequence," (Dec. 1994).

*Primary Examiner*—Charles L. Patterson, Jr.
*Attorney, Agent, or Firm*—Sterne, Kessler, Goldstein & Fox P.L.L.C.

[57] ABSTRACT

A Human amine transporter polypeptide and DNA (RNA) encoding such polypeptide and a procedure for producing such polypeptide by recombinant techniques is disclosed. Also provided are methods for detecting agonists and antagonists to such polypeptide and the use of agonists and antagonists for treating diseases related to the under-expression and over-expression of the Human amine transporter of the present invention. Also disclosed are methods for detecting mutations in the nucleic acid sequence encoding the polypeptide and for detecting altered levels of the soluble form of the polypeptide.

8 Claims, 7 Drawing Sheets

FIG. 1A

```
        10                               30                                    50
TCCTGCGTTATCCCCCTGATTCTGTGGATAACCGTATTNCCGCCTTTGAGTGAGCTGATA
              70                                90                                 110
CCGCTCNCNCAGCCGAACGACCGAGCGCAGCGAGTCAGTGAGCGGAGGAAGCGGAAGAGC
              130                                150                                170
GCCCAATACGCAAACCGCCTCTCCCCGCGCGTTGGCCGATTCATTAATGCAGCTGGCACG
              190                                210                                230
ACAGGTTCCCGACTGGAAAGCGGGCAGTGAGCGCAACGCAATTAATGTGAGTTAGCTCA
              250                                270                                290
CTCATTAGGCACCCCAGGCTTTACACTTTATGCTTCCGGCTCGTATGTTGTGTGGAATTG
              310                                330                                350
TGAGCGGATAACAATTTCACACAGGAAACAGCTATGACCATGATTACGCCAAGCTCGAAA
              370                                390                                410
TTAACCCTCACTAAAGGGAACAAAAGCTGGAGCTCCACCGCGGTGGCGCNCCGCTCTAGAA
              430                                450                                470
CTAGTGGATCCCCCGGNCTGCAGGGAATCCAACATACACAGAATCCAGAATCCTCAGAT
              490                                510                                530
AACAGGAGCAATAAATCCAACAGCACATCCACGTTCAGAGAACAGTGTCCCTGCTGTCT
              550                                570                                590
TGCTAACAGCTGCCAATACCTCACTGAGTGCCTCACACCAACATGGCTCCAAGTGAGTT
              610                                630                                650
TCATTCGTCTGGGCAGACTCCCCTCCCTCTTCCATAAAGGCTGCAGGAGACCTGTAGCTG
              670                                690                                710
TCACAGGACCTTCCCTAAGAGCCCGCAGGGGAAGACTGCCCCAGTCCGGCCATCACCAT
              730                                750                                770                  M
GCTCCGGCCCATTCTGGATGCTCCCCAGCGGTTGCTGAAGGAGGGAGAGCGTCCCGGCA
L  R  P  I  L  D  A  P  Q  R  L  L  K  E  G  R  A  S  R  Q
              790                                810                                830

MATCH WITH FIG. 1B
```

FIG. 1B

MATCH WITH FIG. 1A

```
GCTGGTGCTGGTGGTGGTGTATTCGTCGCTTTGCTCCTGGACAACATGCTGTTTACTGTGGT
 L  V  L  V  V  V  F  V  A  L  L  D  N  M  L  F  T  V  V
850                           870                          890
GGTGCCAATTGTGCCCACCTTCCTATATGACATGGAGTTCAAAGAAGTCATCTCTTCTCT
 V  P  I  V  P  T  F  L  Y  D  M  E  F  K  E  V  I  S  S  L
910                           930                          950
GCACCTCGGGCATGCCGGAAGTTCCCCACATGCCCCTCTCCTGCCTCTTCCACCAT
 H  L  G  H  A  G  S  S  P  H  A  L  A  S  P  A  F  S  T  I
970                           990                         1010
CTTCTCCTTCTTCAACAACACCGTGGCTGTTGAAGAAAGCGTACCTAGTGGAATAGC
 F  S  F  F  N  N  T  V  A  V  E  E  S  V  P  S  G  I  A
1030                          1050                        1070
ATGGATGAATGACACTGCCAGCACCATCCCAGCCCACTGAAGCCATCTCAGCTCA
 W  M  N  D  T  A  S  T  I  P  P  A  T  E  A  I  S  A  H
1090                          1110                        1130
TAAAAACAACTGCTTGCAAGGCACAGGTTTCTTGGAGGAAGAGACTACCCGGGTCGGGGT
 K  N  N  C  L  Q  G  T  G  F  L  E  E  E  T  T  R  V  G  V
1150                          1170                        1190
TCTGTTTGCTTCAAAGGCTGTGATGCAACTTCTGGTCAACCCATTCGTCGTTGGGCCCTCTCAC
 L  F  A  S  K  A  V  M  Q  L  V  N  P  F  V  G  P  L  T
1210                          1230                        1250
CAACAGGATTGGATATCATATCCCCATGTTTGCTGGCTTTGTTATCATGTTTCTCTCCAC
 N  R  I  G  Y  H  I  P  M  F  A  G  F  V  I  M  F  L  S  T
1270                          1290                        1310
AGTTATGTTTGCTTTTTTCTGGGACCTATACTCTACTCTTTGTGGCCCGAACCCTTCAAGG
 V  M  F  A  F  S  G  T  Y  T  L  L  F  V  A  R  T  L  Q  G
1330                          1350                        1370
```

MATCH WITH FIG. 1C

FIG. 1C

MATCH WITH FIG. 1B

```
CATTGGATCTTCATTTCATCTGTTGCAGGTCTTGGAATGCTGGCCAGTGTCTACACTGA
 I  G  S  S  F  S  S  V  A  G  L  G  M  L  A  S  V  Y  T  D
       1390                1410                1430
TGACCATGAGAGAGGACGAGCCATGGGAACTGCTCTGGGGGCCTGGCCTTGGGGTTGCT
 D  H  E  R  G  R  A  M  G  T  A  L  G  G  L  A  L  G  L  L
       1450                1470                1490
GGTGGGAGCTCCCTTTGGAAGTGTAATGTACGAGTTTGTTGGGAAGTCTGCACCCTTCCT
 V  G  A  P  F  G  S  V  M  Y  E  F  V  G  K  S  A  P  F  L
       1510                1530                1550
CATCCTGGCCTTCCTGGCACTACTGGATGGAGCACTCCAGCTTTGCATCCTACAGCCTTC
 I  L  A  F  L  A  L  L  D  G  A  L  Q  L  C  I  L  Q  P  S
       1570                1590                1610
CAAAGTCTCTCCTGAGAGTGCCAAGGGACTCCCCTCTTTATGCTTCTCAAAGACCCTTA
 K  V  S  P  E  S  A  K  G  T  P  L  F  M  L  L  K  D  P  Y
       1630                1650                1670
CATCCTGGTGGCTGCAGGGTCCATCTGCTTTGCCAACATGGGGGTGGCCATCCTGGAGCC
 I  L  V  A  A  G  S  I  C  F  A  N  M  G  V  A  I  L  E  P
       1690                1710                1730
CACACTGCCCATCTGGATGATGCAGACCATGTGCTCCCCCAAGTGGCAGCTGGGTCTAGC
 T  L  P  I  W  M  M  Q  T  M  C  S  P  K  W  Q  L  G  L  A
       1750                1770                1790
TTTCTTGCCTGCCAGTGTGTCCTACCTGTGTCCTGTTCCCTAATCGGATGCTGGTGGCCAA
 F  L  P  A  S  V  S  Y  L  I  G  T  N  L  F  G  V  L  A  N
       1810                1830                1850
CAAGATGGGTCGGTGGCTGTGTGGCTGTGTTCCTCACAAAATTTTGTCTTCATTGGCCCCAATGCAGGCTTGCT
 K  M  G  R  W  L  C  S  L  I  G  M  L  V  V  G  T  S  L  L
       1870                1890                1910
CTGTGTTCCTCTGGCTCACAAAATTTTGTCTCATTGGCCCCAATGCAGGGCTTGGCCT
```

MATCH WITH FIG. 1D

FIG. 1D

MATCH WITH FIG. 1C

```
  C   V   P   L   A   H   H   K   N   F   G   L   I   G   P   N   A   G   L   G   L
                1930                        1950                        1970
TNCCATAGGCATGGTGGAATCTTCTATGATGCCCATCATGGGGCCACCTGGTGGATCCACG
  X   I   G   M   V   E   S   S   M   M   P   I   M   G   H   L   V   D   P   R
                1990                        2010                        2030
CCACACCTCGGTGTATGGGAGTGTCCACGCCGATCGCTGATGTGGCTTTTTGCATGGGCTT
  H   T   S   V   Y   G   S   V   H   A   I   A   D   V   A   F   C   M   G   F
                2050                        2070                        2090
TGCTATAGGCTATTCTGAGTCAGGAGACTGCCCCATGGAGACCCGGATGTATCAACCCAGAA
  A   I   G   Y   S   E   S   G   L   P   H   G   D   D   P   D   V   S   T   Q   K
                2110                        2130                        2150
ACCTCTTCCCTGGACCACCAGTCACCATGGCTGACCCACGGCTCAGTGCCCTCAAAACCTCTG
  P   L   P   W   T   S   H   H   G   *
                2170                        2190                        2210
CCTGGGATCTTCTTCCCTCCCCCATGGACACTGTCCCTGATACTCTTCTCACCTGTGT
                2230                        2250                        2270
AACTTGTAGCTCTTCMTCTATGCCTTGGTGCCGCAGTGGCCCATCTTTTATGGAAGACA
                2290                        2310                        2330
GAGTGATGCACCYYCCCGCTGTGTGAGGTTGATTAAACTTGAGCTGTGACGGGGTTCTG
                2350                        2370                        2390
CAAGGGGTGACTCATTGYATAGAGGTGGTAGTGAGTAATGTGCCCTGAAACCAGTGGGG
                2410                        2430                        2450
TGACTGACAAGCCCTCTTTAATCTGTTGCCTGATTTTCTCTGGCATAGCCCCAACAGATCG
                2470                        2490                        2510
GAAGAGTGTTACCCTCTTTWCCCTCAACGTGTCTTCCCGGTTTTCCCCAGCCGAGTT
```

MATCH WITH FIG. 1E

FIG. 1E

MATCH WITH FIG. 1D

```
2530                     2550                      2570
GAGAAAATGTTCTCAGCATTGTCTTGCTGCCAAATGCCAGCKTGAAGAGTTWGGTATGKT
         2590                     2610                     2630
TTTCTNCCATTTATTTTATTTATTWACTAAAGTGAATGATTTTACTGTGGYTAAATCTA
         2650                     2670                     2690
GAGCTGCTAAAGGGCTTTACCCTCAGTGAAAAGTGTCTTCTATTTNCATWATCTTTCAG
         2710                     2730                     2750
AAACWGGAGCCCATTTCTCTTCTGGTGGAGTTATNGACATCCTCCTGACCNCCCCTGTGT
         2770                     2790                     2810
NTNCCTACCTNTACTGAACCTCTTAGACTCTNAGAAATAAAAGTAGAAAGAAGACAGAAA
         2830                     2850                     2870
AATTAACTGATTAGACCCAAGATTTCATGGGAAGAAGTTAAAAGAAACTGCCTTGGAAAT

CCCTC
```

FIG. 2A

Homology Alignment between HATBG78 and
the Rat Amine Transporter

```
  1 MLRPILDAPQRLLKEGRASRQLVLVVVFVALLLDNMLFTVVVPIVPTFLY  50
    ||...:||||||||||.||..:||.||||||||||||:|||||||||||
  1 MLQVVLGAPQRLLKEGRQSRKLVLVVVFVALLLDNMLLTVVVPIVPTFLY  50

51 DMEFKEVISSLHLGHAGSSPHALASPAFSTIFSFFNNNTVAVEESVPSGI 100
    ||||  |||  ||.|||.:||.:||.|||||||.|...||..|||  :
 51 ATEFKDSNSSLHRGPSVSSQQALTSPAFSTIFSFFDNTTTTVEEHVPFRV 100

101 AWMNDTASTIPPPATEAISAHKNNCLQGTGFLEEETTRVGVLFASKAVMQ 150
    .|   |.:||.|||  |...:..||   |:|||||||..|:|:|||||:||
101 TW...TNGTIPPPVTEASSVPKNNCLQGIEFLEEENVRIGILFASKALMQ 147

151 LLVNPFVGPLTNRIGYHIPMFAGFVIMFLSTVMFAFSGTYTLLFVARTLQ 200
    ||||||||||||||||||||||.|:||||||.||||||||| ||.||||||
148 LLVNPFVGPLTNRIGYHIPMFVGFMIMFLSTLMFAFSGTYALLFVARTLQ 197

201 GIGSSFSSVAGLGMLASVYTDDHERGRAMGTALGGLALGLLVGAPFGSVM 250
    ||||||||||||||||||||||..:||||||||:||||||||||||||||||
198 GIGSSFSSVAGLGMLASVYTDNYERGRAMGIALGGLALGLLVGAPFGSVM 247
```

MATCH WITH FIG. 2B

FIG. 2B

MATCH WITH FIG. 2A

```
251 YEFVGKSAPFLILAFLALLDGALQLCILQPSKVSPESAKGTPLFMLLKDP 300
    |||||||| ||||||||||||||||||||| |||||||| | |.|: |||||
248 YEFVGKSSPFLILAFLALLDGALQLCILWPSKVSPESAMGTSLLTLLKDP 297

301 YILVAAGSICFANMGVAILEPTLPIWMMQTMCSPKWQLGLAFLPASVSYL 350
    |||||||||| ||||||||||||||||||||||||| |||||||||| ||
298 YILVAAGSICLANMGVAILEPTLPIWMMQTMCSPEWQLGLAFLPASVAYL 347

351 IGTNLFGVLANKMGRWLCSLIGMLVVGTSLLCVPLAHKNFGLIGPNAGLG 400
    |||||||||||||||||||:||:|| :||:|||||||| |.||||||||||
348 IGTNLFGVLANKMGRWLCSLVGMVAVGISLLCVPLAHNIFGLIGPNAGLG 397

401 LXIGMVESSMMPIMGHLVDPRHTSVYGSVHAIADVAFCMGFAIGYSESGL 450
    : .||||| ::|| :.|||| .||| ||||||||||||| | |||| |..:.|
398 FAIGMVDSSLMPIMGYLVDLRHTSVYGSVYAIADVAFCVGFAIGPSTGGV 447

451 PHGDPDVSTQKPLPWTSH 468
    . : :..:.: | :
448 IVQVIGFPWLMVIIGTIN 465
```

5,859,200

HUMAN AMINE TRANSPORTER

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human amine transporter. The invention also relates to inhibiting the action of such polypeptides.

RELATED ART

Neurosensory and neuromotor functions are carried out by neurotransmission. Neurotransmission is the conductance of a nerve impulse from one neuron, called the presynaptic neuron, to another neuron, called the postsynaptic neuron, across the synaptic cleft. Transmission of the nerve impulse across the synaptic cleft involves the secretion of neurotransmitter substances. The neurotransmitter is packaged into vesicles in the presynaptic neuron and released into the synaptic cleft to find its receptor at the postsynaptic neuron. Transmission of the nerve impulse is normally transient.

An essential property of synaptic transmission is the rapid termination of action following neurotransmitter release. For many neurotransmitters, including catecholamine, serotonin, and certain amino acids (e.g., gamma-aminobutyric acid (GABA), glutamate and glycine), rapid termination of synaptic action is achieved by the uptake of the neurotransmitter into the presynaptic terminal and surrounding glial cells. This rapid re-accumulation of a neurotransmitter is the result of re-uptake by the presynaptic terminals.

At presynaptic terminals, the various molecular structures for re-uptake are highly specific for such neurotransmitters as choline and the biogenic amines (low molecular weight neurotransmitter substances such as dopamine, norepinephrine, epinephrine, serotonin and histamine). These molecular apparatuses are termed transporters. These transporters move neurotransmitter substances from the synaptic cleft back across the cell membrane of the presynaptic neuron into the cytoplasm of the presynaptic terminus and therefore terminate the function of these substances. Inhibition or stimulation of neurotransmitter uptake provides a means for modulating the effects of the endogenous neurotransmitters.

Re-uptake of neurotransmitter substances by the transporters may be sodium-dependent. For instance, the GABA transporter is a member of the recently described sodium-dependent neurotransmitter transporter gene family. These transporters are transmembrane receptor complexes having an extracellular portion, a transmembrane portion and an intracellular portion. A significant degree of homology exists in the transmembrane domains of the entire family of sodium-dependent neurotransmitter transporter proteins, with considerable stretches of identical amino acids, while much less homology is apparent in the intracellular and extracellular loops connecting these domains. The extracellular loop in particular seems to be unique for each transporter. This region may contribute to substrate and/or inhibitor specificities.

Identifying the novel amine transporter of the present invention and elucidating the structural and functional distinctions between different types of transporters is important in understanding the cellular and molecular bases of behavior and disease.

SUMMARY OF THE INVENTION

The polypeptide of the present invention has been putatively identified as an amine transporter. This identification has been made as a result of amino acid sequence homology to the rat amine transporter.

In accordance with one aspect of the present invention, there is provided a novel mature polypeptide which is a human amine transporter, as well as biologically active and diagnostically or therapeutically useful fragments, analogs and derivatives thereof.

In accordance with another aspect of the present invention, there are provided isolated nucleic acid molecules encoding a human amine transporter, including mRNAs, DNAs, cDNAs, genomic DNAs as well as analogs and biologically active and diagnostically or therapeutically useful fragments and derivatives thereof.

In accordance with yet a further aspect of the present invention, there is provided a process for producing such polypeptide by recombinant techniques comprising culturing recombinant prokaryotic and/or eukaryotic host cells, containing a human amine transporter nucleic acid sequence, under conditions promoting expression of said protein and subsequent recovery of said protein.

In accordance with yet a further aspect of the present invention, there is provided a process for utilizing such polypeptide, or polynucleotide encoding such polypeptide for screening for agonists and antagonists and ligands to such polypeptide.

In accordance with yet a further aspect of the present invention, there is provided a method for utilizing such agonists for stimulating the amine transporter uptake of neurotransmitter ligands for the treatment of diseases related to under-expression of the amine transporter or over-expression of the ligand.

In accordance with yet another aspect of the present invention, there is also provided a process for using antagonists for inhibiting the amine transporter uptake of neurotransmitter ligands for the treatment of diseases related to over-expression of the amine transporter or under-expression of the ligand.

In accordance with yet a further aspect of the present invention, there are provided antibodies against such polypeptides.

In accordance with yet a further aspect of the present invention, there are also provided nucleic acid probes comprising nucleic acid molecules of sufficient length to specifically hybridize to human amine transporter sequences.

In accordance with still another aspect of the present invention, there are provided diagnostic assays for detecting diseases related to the under-expression and over-expression of the amine transporter polypeptide and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A–1E illustrate the cDNA sequence (SEQ. ID NO:1) and corresponding deduced amino acid sequence (SEQ. ID NO:2) of the human amine transporter of the present invention. The standard one-letter abbreviations for amino acids are used. Sequencing was performed using a 373 Automated DNA sequencer (Applied Biosystems, Inc.). Sequencing accuracy is predicted to be greater than 97% accurate.

FIGS. 2A–2B are an illustration of an amino acid homology alignment between the amine transporter and a rat amine transporter (SEQ ID NO:2) (retrieved from Genbank public database).

BRIEF DESCRIPTION OF THE INVENTION

The amine transporter (SEQ ID NO:9) of the present invention may be responsible for re-uptake of one or any of the amine neurotransmitters present in mammalian cells. Examples of such amine transporters include dopamine, norepinephrine, epinephrine, serotonin and histamine, and other amino acid transmitters, including GABA, glycine and glutamate.

In accordance with an aspect of the present invention, there is provided an isolated nucleic acid (polynucleotide) which encodes for the mature polypeptide having the deduced amino acid sequence of FIG. 1 (SEQ ID No. 2) or for the mature polypeptide encoded by the cDNA of the clone deposited as ATCC Deposit No. 75980 on Dec. 16, 1994 at the American Type Culture Collection, 12301 Parklawn Drive, Rockville, Md. 20852.

A polynucleotide encoding a polypeptide of the present invention may be obtained from a variety of human tissues. The polynucleotide of this invention was discovered in a cDNA library derived from a human adrenal gland tumor. It is structurally related to the amine transporter family. It contains an open reading frame encoding a protein of 470 amino acid residues. The protein exhibits the highest degree of homology to the rat amine transporter with 80% identity and 86% similarity over a 468 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID No. 2) or that of the deposited clone or may be a different coding sequence which coding sequence, as a result of the redundancy or degeneracy of the genetic code, encodes the same mature polypeptide as the DNA of FIG. 1 (SEQ ID No. 2) or the deposited cDNA.

The polynucleotide which encodes for the mature polypeptide of FIG. 1 (SEQ ID No. 2) or for the mature polypeptide encoded by the deposited cDNA may include only the coding sequence for the mature polypeptide or the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID No. 2) or the same mature polypeptide encoded by the cDNA of the deposited clone as well as variants of such polynucleotides which variants encode for a fragment, derivative or analog of the polypeptide of FIG. 1 (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID No. 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 (SEQ ID No. 1) or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a human amine transporter polypeptide which has the deduced amino acid sequence of FIG. 1 (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the human amine transporter genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudo-rabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, HEK, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HEK, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements.

The human amine transporter polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Fragments of the full length human amine transporter gene may be used as a hybridization probe for a cDNA library to isolate the full length gene and to isolate other genes which have a high sequence similarity to the gene or similar biological activity. Probes of this type generally have at least 20 bases. Preferably, however, the probes have at least 30 bases and generally do not exceed 50 bases, although they may have a greater number of bases. The probe may also be used to identify a cDNA clone corresponding to a full length transcript and a genomic clone or clones that contain the complete human amine transporter gene including regulatory and promotor regions, exons, and introns. As an example of a screen comprises isolating the coding region of the human amine transporter gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides a method for determining amine neurotransmitters which are transported by the human amine transporter of the present invention. An example of an assay which will identify these neurotransmitters comprises infecting mammalian cells with recombinant vaccinia virus strain VTF-7 encoding a T7 RNA polymerase and following such infection with liposome-mediated transfection with the amine transporter gene through the use of a vector, for example, pBSSKII(−). Controlled transfections are also done with equivalent amounts of vector alone. Assays are performed eight hours following transfection in modified Krebs-Ringer-HEPES buffer. Cells are then incubated with [$^3$H] neurotransmitter (for example, GABA, dopamine, serotonin, etc.). Uptake is stopped by placing the cells on ice. Cells are solubilized in one percent SDS, and the amount of radioactivity accumulated is determined by liquid scintillation counting. A significant amount of uptake determines that the particular neurotransmitter is taken up by the human amine transporter of the present invention by determining background using control transfections with pBSSKII for each assay and subtracting the values obtained from the signals determined for the specific amine neurotransmitters.

This invention also provides a method of detecting expression of an amine transporter on the surface of a cell by detecting the presence of mRNA coding for an amine transporter. This method comprises obtaining total mRNA from the cell using methods well-known in the art and contacting the mRNA so obtained with a nucleic acid probe of at least 15 nucleotides and which is capable of specifically hybridizing with a sequence included within the sequence of a nucleic acid molecule encoding a human amine transporter, under hybridizing conditions, detecting the presence of mRNA hybridized to the probe, and thereby detecting the expression of the amine transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those of skill in the art.

Alternatively, an antibody directed to the human amine transporter may be employed under conditions permitting binding of the antibody to the transporter, and detecting the presence of the transporter on the surface of the cell. Such a method may be employed for determining whether a given cell is defective in expression of the amine transporter. Detection methods include fluorescent markers bound to the antibodies.

The invention also provides a method for determining whether a compound not known to be capable of specifically binding to a human amine transporter can specifically bind to the human amine transporter, which comprises contacting a mammalian cell comprising a plasmid adapted for expression in a mammalian cell which plasmid further comprises a DNA which expresses the amine transporter on the cell surface with the compound under conditions permitting binding of ligands known to bind to the amine transporter, detecting the presence of any compound bound to the mammalian amine transporter, the presence of bound compound indicating that the compound is capable of specifically binding to the human amine transporter.

This invention also provides a method of screening drugs to identify drugs which specifically interact with, and bind to a human amine transporter on the surface of a cell which comprises contacting a mammalian cell which expresses the human amine transporter on the surface of a cell with a plurality of drugs, detecting those drugs which bind to the cell, and thereby identifying drugs which specifically interact with, and bind to, the human amine transporter.

The present invention further provides a method for identifying agonist or antagonist compounds to the human amine transporter of the present invention by the employment of competition assays. An example of such an assay for identifying antagonists comprises contacting a neuronal cell which expresses the human amine transporter on the surface thereof with a known neurotransmitter, in the presence of a potential compound to determine the amount of neurotransmitter transported. Controls may also be prepared in the absence of the potential compound and the amount of amine neurotransmitter transported by the cell upon comparison to the control cell indicates if the potential compound stimulated transport or inhibited transport of the labeled amine neurotransmitter by the transfected mammalian cell.

Examples of human amine transporter antagonists include an antibody directed to the human amine transporter which comprises, for example, a monoclonal antibody directed to an epitope of a human amine transporter present on the surface of the cell. These antibodies are useful to detect the presence of human amine transporters or to inhibit the function of the transporters in humans.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix— see Lee et al., Nucl. Acids Res., 6:3073 (1979); Cooney et al, Science, 241:456 (1988); and Dervan et al., Science, 251:1360 (1991)), thereby preventing transcription and the production of human amine transporter. The antisense RNA oligonucleotide hybridizes to the mRNA in vivo and blocks translation of the mRNA molecule into the human amine transporter polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of human amine transporter.

Potential antagonists also include a soluble form of a human amine transporter, e.g. a fragment of the transporter, which binds to the neurotransmitter and prevents it from interacting with the human amine transporter.

Potential antagonists further include a small molecule which binds to and occupies the extracellular portion of the human amine transporter thereby making the human amine transporter inaccessible to the neurotransmitter such that transport is inhibited. Examples of small molecules include but are not limited to small peptides or peptide-like molecules.

This invention additionally provides a method of treating an abnormal condition related to an excess of amine transporter activity which comprises administering to a subject the antagonist as hereinabove described along with a pharmaceutically acceptable carrier in an amount effective to block binding of naturally occurring substrates to the amine transporters and thereby alleviate the abnormal condition. Examples of abnormal conditions include epilepsy, schizophrenia, depression, cognitive impairment, anxiety and migraine headaches.

The invention also provides a method of treating abnormal conditions related to an under-expression of amine transporter activity which comprises administering to a subject an amount of the agonist described above in combination with a pharmaceutically acceptable carrier, in an amount effective to enhance binding of naturally occuring substrates to the amine transporter and thereby alleviate the abnormal conditions. Some examples of abnormal conditions are Parkinson's disease and Alzheimer's disease.

The soluble form of the human amine transporter, and agonists and antagonists may be employed in combination with a suitable pharmaceutical carrier. Such compositions comprise a therapeutically effective amount of the transporter, agonist or antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The human amine transporter and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

This invention is also related to the use of the human amine transporter gene as part of a diagnostic assay for detecting diseases or susceptibility to diseases related to the presence of mutations in the human amine transporter genes. Such diseases are related to under-expression of the human amine transporter.

Individuals carrying mutations in the human amine transporter gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the human amine transporter protein can be used to identify and analyze human amine transporter mutations. For example, deletions and insertions can be detected by a change in size of the amplified product in comparison to the normal genotype. Point mutations can be identified by hybridizing amplified DNA to radiolabeled human amine transporter RNA or alternatively, radiolabeled human amine transporter antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, U.S.A., 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the expression sequence tag was derived, and the longer the Better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLES

Example 1
Bacterial Expression and Purification of Human Amine Transporter

The DNA sequence encoding human amine transporter, ATCC # 75980, is initially amplified using PCR oligonucleotide primers corresponding to the 5' and 3' end sequences of the processed amine transporter nucleic acid sequence (minus the signal peptide sequence). Additional nucleotides corresponding to amine transporter gene are added to the 5' and 3' sequences respectively. The 5' oligonucleotide primer has the sequence 5' GACTAAAGCTTAATGCTCCGGC-CCATTCTG 3' (SEQ ID No. 3) contains a HindIII restriction enzyme site followed by 18 nucleotides of human amine transporter coding sequence starting from the presumed terminal amino acid of the processed protein. The 3' sequence 5' GAACTTCTAGACGGTCAGCCATGGT-GACTGG 3' (SEQ ID No. 4) contains complementary sequences to an XbaI site and is followed by 20 nucleotides of the human amine transporter gene. The X restriction enzyme sites correspond to the restriction enzyme sites on the bacterial expression vector pQE-9 (Qiagen, Inc. Chatsworth, Calif.). pQE-9 encodes antibiotic resistance (AMp$^r$), a bacterial origin of replication (ori), an IPTG-regulatable promoter operator (P/O), a ribosome binding site (RBS), a 6-His tag and restriction enzyme sites. pQE-9 is then digested with HindIII and XbaI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized human amine transporter is purified from this solution by chromatography on a Nickel-Chelate column under conditions that allow for tight binding by proteins containing the 6-His tag (Hochuli, E. et al., J. Chromatography 411:177–184 (1984)). Human amine transporter protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

Example 2
Cloning and expression of human amine transporter using the baculovirus expression system The DNA sequence encoding the full length human amine transporter protein, ATCC # 75980, is amplified using PCR oligonucleotide primers corresponding to the 5' and 3' sequences of the gene:

The 5' primer has the sequence 5' CGGGATCCCTCC ATGGCT CCGGCCCATTCTG 3' (SEQ ID No. 5) and contains a BamHI restriction enzyme site (in bold) followed by 4 nucleotides resembling an efficient signal for the initiation of translation in eukaryotic cells (Kozak, M., J. Mol. Biol., 196:947–950 (1987) which is just behind the first 18 nucleotides of the human amine transporter gene (the initiation codon for translation "ATG" is underlined).

The 3' primer has the sequence 5' CGGGATCCCGCT CAGCCATGGTGACTGGT 3' (SEQ ID No. 6) and contains the cleavage site for the restriction endonuclease BamHI and 18 nucleotides complementary to the 3' non-translated sequence of the human amine transporter gene. The amplified sequences are isolated from a 1% agarose gel using a commercially available kit ("Geneclean," BIO 101 Inc., La Jolla, Calif.). The fragment is then digested with the endonucleases BamHI and then purified again on a 1% agarose gel. This fragment is designated F2.

The vector pRG1 (modification of pVL941 vector, discussed below) is used for the expression of the human amine transporter protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of PRG1 such as pAc373, pVL941 and pAcIM1 (Luckow, V. A. and Summers, M. D., Virology, 170:31–39).

The plasmid is digested with the restriction enzymes BamHI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E.coli* HB 101 cells are then transformed and bacteria identified that contained the plasmid (pBac-Human amine transporter) with the human amine transporter gene using the enzyme BamHI. The sequence of the cloned fragment is confirmed by DNA sequencing.

5 μg of the plasmid pBac-Human amine transporter is co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. U.S.A., 84:7413–7417 (1987)).

1 μg of BaculoGold™ virus DNA and 5 μg of the plasmid pBac-Human amine transporter are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10)

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-Human amine transporter at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

Example 3

Expression of Recombinant Human Amine Transporter in COS cells

The expression of plasmid, Human amine transporter HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire Human amine transporter precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, et al., Cell, 37:767, (1984)). The infusion of HA tag to the target protein allows easy detection of the recombinant protein with an antibody that recognizes the HA epitope.

The plasmid construction strategy is described as follows:

The DNA sequence encoding Human amine transporter, ATCC # 75980, is constructed by PCR using two primers: the 5' primer 5' GTCCAAGCTTGCCACCATGCTGCGGC-CCATTCTG 3' (SEQ ID No. 7) contains a HindIII site followed by 18 nucleotides of Human amine transporter coding sequence starting from the initiation codon; the 3' sequence 5' CTAGCTCGAGTCAGCCATGG TGACTGG-TAGCGTAGTCTGGGACGTCGTATGGGTAGCA 3' (SEQ ID No. 8) contains complementary sequences to an XhoI site, translation stop codon, HA tag and the last 18 nucleotides of the Human amine transporter coding sequence (not including the stop codon). Therefore, the PCR product contains a HindIII site, human amine transporter coding sequence followed by HA tag fused in frame, a translation termination stop codon next to the HA tag, and an HindIII site. The PCR amplified DNA fragment and the vector, pcDNAI/Amp, are digested with HindIII and XhoI restriction enzyme and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant amine transporter, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the Human amine transporter HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

Example 4

Expression pattern of Human amine transporter in human tissue

Northern blot analysis is carried out to examine the levels of expression of Human amine transporter in human tissues. Total cellular RNA samples are isolated with RNAzol™ B system (Biotecx Laboratories, Inc. Houston, Tex.). About 10 μg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column (5 Prime–3 Prime, Inc. Boulder, Colo.). The filter is then hybridized with radioactive labeled full length Human amine transporter gene at 1,000,000 cpm/ml in 0.5M NaPO$_4$, pH 7.4 and 7% SDS overnight at 65° C. After wash twice at room temperature and twice at 60° C. with 0.5× SSC, 0.1% SDS, the filter is then exposed at −70° C. overnight with an intensifying screen.

Numerous modifications and variations of the present invention are possible in light of the above teachings and, therefore, within the scope of the appended claims, the invention may be practiced otherwise than as particularly described.

---

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2885 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 719..2128

( x i ) SEQUENCE DESCRIPTION: SEQ ID NO:1:

```
TCCTGCGTTA  TCCCCCTGAT  TCTGTGGATA  ACCGTATTNC  CGCCTTTGAG  TGAGCTGATA      60

CCGCTCNCCN  CAGCCGAACG  ACCGAGCGCA  GCGAGTCAGT  GAGCGAGGAA  GCGGAAGAGC     120

GCCCAATACG  CAAACCGCCT  CTCCCCGCGC  GTTGGCCGAT  TCATTAATGC  AGCTGGCACG     180

ACAGGTTTCC  CGACTGGAAA  GCGGGCAGTG  AGCGCAACGC  AATTAATGTG  AGTTAGCTCA     240

CTCATTAGGC  ACCCCAGGCT  TTACACTTTA  TGCTTCCGGC  TCGTATGTTG  TGTGGAATTG     300

TGAGCGGATA  ACAATTTCAC  ACAGGAAACA  GCTATGACCA  TGATTACGCC  AAGCTCGAAA     360

TTAACCCTCA  CTAAAGGGAA  CAAAAGCTGG  AGCTCCACCG  CGGTGGCGNC  CGCTCTAGAA     420

CTAGTGGATC  CCCCGGNCTG  CAGGGGCACA  CACACGCACA  CATACACAGA  ATCCTCAGAT     480

AACAGGAGGC  AATAAATCCA  ACAGCACATC  CACGTTCAGA  GAACAGTGTC  CCTGCTGTCT     540

TGCTAACAGC  TGCCAATACC  TCACTGAGTG  CCTCACACCA  ACATGGGCTC  CAAGTGAGTT     600

TCATTCGTCT  GGGCAGACTC  CCTCCCCTCT  TCCATAAAGG  CTGCAGGAGA  CCTGTAGCTG     660

TCACAGGACC  TTCCCTAAGA  GCCCGCAGGG  GGAAGACTGC  CCCAGTCCGG  CCATCACC      718
```

| ATG | CTC | CGG | CCC | ATT | CTG | GAT | GCT | CCC | CAG | CGG | TTG | CTG | AAG | GAG | GGG | 766 |
|---|---|---|---|---|---|---|---|---|---|---|---|---|---|---|---|---|
| Met | Leu | Arg | Pro | Ile | Leu | Asp | Ala | Pro | Gln | Arg | Leu | Leu | Lys | Glu | Gly | |
| 1 | | | | 5 | | | | | 10 | | | | | 15 | | |

| AGA | GCG | TCC | CGG | CAG | CTG | GTG | CTG | GTG | GTG | GTA | TTC | GTC | GCT | TTG | CTC | 814 |
|---|---|---|---|---|---|---|---|---|---|---|---|---|---|---|---|---|
| Arg | Ala | Ser | Arg | Gln | Leu | Val | Leu | Val | Val | Val | Phe | Val | Ala | Leu | Leu | |
| | | | 20 | | | | | 25 | | | | | 30 | | | |

| CTG | GAC | AAC | ATG | CTG | TTT | ACT | GTG | GTG | GTG | CCA | ATT | GTG | CCC | ACC | TTC | 862 |
|---|---|---|---|---|---|---|---|---|---|---|---|---|---|---|---|---|
| Leu | Asp | Asn | Met | Leu | Phe | Thr | Val | Val | Val | Pro | Ile | Val | Pro | Thr | Phe | |
| | | 35 | | | | | 40 | | | | | 45 | | | | |

| CTA | TAT | GAC | ATG | GAG | TTC | AAA | GAA | GTC | ATC | TCT | TCT | CTG | CAC | CTC | GGG | 910 |
|---|---|---|---|---|---|---|---|---|---|---|---|---|---|---|---|---|
| Leu | Tyr | Asp | Met | Glu | Phe | Lys | Glu | Val | Ile | Ser | Ser | Leu | His | Leu | Gly | |
| | 50 | | | | | 55 | | | | | 60 | | | | | |

| CAT | GCC | GGA | AGT | TCC | CCA | CAT | GCC | CTC | GCC | TCT | CCT | GCC | TTT | TCC | ACC | 958 |
|---|---|---|---|---|---|---|---|---|---|---|---|---|---|---|---|---|
| His | Ala | Gly | Ser | Ser | Pro | His | Ala | Leu | Ala | Ser | Pro | Ala | Phe | Ser | Thr | |
| 65 | | | | | 70 | | | | | 75 | | | | | 80 | |

| ATC | TTC | TCC | TTC | TTC | AAC | AAC | AAC | ACC | GTG | GCT | GTT | GAA | GAA | AGC | GTA | 1006 |
|---|---|---|---|---|---|---|---|---|---|---|---|---|---|---|---|---|
| Ile | Phe | Ser | Phe | Phe | Asn | Asn | Asn | Thr | Val | Ala | Val | Glu | Glu | Ser | Val | |
| | | | | 85 | | | | | 90 | | | | | 95 | | |

| CCT | AGT | GGA | ATA | GCA | TGG | ATG | AAT | GAC | ACT | GCC | AGC | ACC | ATC | CCA | CCT | 1054 |

```
                Pro  Ser  Gly  Ile  Ala  Trp  Met  Asn  Asp  Thr  Ala  Ser  Thr  Ile  Pro  Pro
                               100                      105                      110

CCA  GCC  ACT  GAA  GCC  ATC  TCA  GCT  CAT  AAA  AAC  AAC  TGC  TTG  CAA  GGC                 1102
Pro  Ala  Thr  Glu  Ala  Ile  Ser  Ala  His  Lys  Asn  Asn  Cys  Leu  Gln  Gly
               115                      120                      125

ACA  GGT  TTC  TTG  GAG  GAA  GAG  ACT  ACC  CGG  GTC  GGG  GTT  CTG  TTT  GCT                 1150
Thr  Gly  Phe  Leu  Glu  Glu  Glu  Thr  Thr  Arg  Val  Gly  Val  Leu  Phe  Ala
               130                      135                      140

TCA  AAG  GCT  GTG  ATG  CAA  CTT  CTG  GTC  AAC  CCA  TTC  GTG  GGC  CCT  CTC                 1198
Ser  Lys  Ala  Val  Met  Gln  Leu  Leu  Val  Asn  Pro  Phe  Val  Gly  Pro  Leu
145                 150                      155                           160

ACC  AAC  AGG  ATT  GGA  TAT  CAT  ATC  CCC  ATG  TTT  GCT  GGC  TTT  GTT  ATC                 1246
Thr  Asn  Arg  Ile  Gly  Tyr  His  Ile  Pro  Met  Phe  Ala  Gly  Phe  Val  Ile
                         165                      170                      175

ATG  TTT  CTC  TCC  ACA  GTT  ATG  TTT  GCT  TTT  TCT  GGG  ACC  TAT  ACT  CTA                 1294
Met  Phe  Leu  Ser  Thr  Val  Met  Phe  Ala  Phe  Ser  Gly  Thr  Tyr  Thr  Leu
               180                      185                      190

CTC  TTT  GTG  GCC  CGA  ACC  CTT  CAA  GGC  ATT  GGA  TCT  TCA  TTT  TCA  TCT                 1342
Leu  Phe  Val  Ala  Arg  Thr  Leu  Gln  Gly  Ile  Gly  Ser  Ser  Phe  Ser  Ser
               195                      200                      205

GTT  GCA  GGT  CTT  GGA  ATG  CTG  GCC  AGT  GTC  TAC  ACT  GAT  GAC  CAT  GAG                 1390
Val  Ala  Gly  Leu  Gly  Met  Leu  Ala  Ser  Val  Tyr  Thr  Asp  Asp  His  Glu
          210                      215                      220

AGA  GGA  CGA  GCC  ATG  GGA  ACT  GCT  CTG  GGG  GGC  CTG  GCC  TTG  GGG  TTG                 1438
Arg  Gly  Arg  Ala  Met  Gly  Thr  Ala  Leu  Gly  Gly  Leu  Ala  Leu  Gly  Leu
225                 230                      235                           240

CTG  GTG  GGA  GCT  CCC  TTT  GGA  AGT  GTA  ATG  TAC  GAG  TTT  GTT  GGG  AAG                 1486
Leu  Val  Gly  Ala  Pro  Phe  Gly  Ser  Val  Met  Tyr  Glu  Phe  Val  Gly  Lys
               245                      250                      255

TCT  GCA  CCC  TTC  CTC  ATC  CTG  GCC  TTC  CTG  GCA  CTA  CTG  GAT  GGA  GCA                 1534
Ser  Ala  Pro  Phe  Leu  Ile  Leu  Ala  Phe  Leu  Ala  Leu  Leu  Asp  Gly  Ala
               260                      265                      270

CTC  CAG  CTT  TGC  ATC  CTA  CAG  CCT  TCC  AAA  GTC  TCT  CCT  GAG  AGT  GCC                 1582
Leu  Gln  Leu  Cys  Ile  Leu  Gln  Pro  Ser  Lys  Val  Ser  Pro  Glu  Ser  Ala
               275                      280                      285

AAG  GGG  ACT  CCC  CTC  TTT  ATG  CTT  CTC  AAA  GAC  CCT  TAC  ATC  CTG  GTG                 1630
Lys  Gly  Thr  Pro  Leu  Phe  Met  Leu  Leu  Lys  Asp  Pro  Tyr  Ile  Leu  Val
               290                      295                      300

GCT  GCA  GGG  TCC  ATC  TGC  TTT  GCC  AAC  ATG  GGG  GTG  GCC  ATC  CTG  GAG                 1678
Ala  Ala  Gly  Ser  Ile  Cys  Phe  Ala  Asn  Met  Gly  Val  Ala  Ile  Leu  Glu
305                 310                      315                           320

CCC  ACA  CTG  CCC  ATC  TGG  ATG  ATG  CAG  ACC  ATG  TGC  TCC  CCC  AAG  TGG                 1726
Pro  Thr  Leu  Pro  Ile  Trp  Met  Met  Gln  Thr  Met  Cys  Ser  Pro  Lys  Trp
               325                      330                      335

CAG  CTG  GGT  CTA  GCT  TTC  TTG  CCT  GCC  AGT  GTG  TCC  TAC  CTC  ATT  GGC                 1774
Gln  Leu  Gly  Leu  Ala  Phe  Leu  Pro  Ala  Ser  Val  Ser  Tyr  Leu  Ile  Gly
               340                      345                      350

ACC  AAC  CTC  TTT  GGT  GTG  TTG  GCC  AAC  AAG  ATG  GGT  CGG  TGG  CTG  TGT                 1822
Thr  Asn  Leu  Phe  Gly  Val  Leu  Ala  Asn  Lys  Met  Gly  Arg  Trp  Leu  Cys
               355                      360                      365

TCC  CTA  ATC  GGG  ATG  CTG  GTA  GTA  GGT  ACC  AGC  TTG  CTC  TGT  GTT  CCT                 1870
Ser  Leu  Ile  Gly  Met  Leu  Val  Val  Gly  Thr  Ser  Leu  Leu  Cys  Val  Pro
               370                      375                      380

CTG  GCT  CAC  AAA  AAT  TTT  GGT  CTC  ATT  GGC  CCC  AAT  GCA  GGG  CTT  GGC                 1918
Leu  Ala  His  Lys  Asn  Phe  Gly  Leu  Ile  Gly  Pro  Asn  Ala  Gly  Leu  Gly
385                 390                      395                           400

CTT  NCC  ATA  GGC  ATG  GTG  GAA  TCT  TCT  ATG  ATG  CCC  ATC  ATG  GGG  CAC                 1966
Leu  Xaa  Ile  Gly  Met  Val  Glu  Ser  Ser  Met  Met  Pro  Ile  Met  Gly  His
                         405                      410                      415

CTG  GTG  GAT  CCA  CGC  CAC  ACC  TCG  GTG  TAT  GGG  AGT  GTC  CAC  GCC  ATC                 2014
```

```
Leu  Val  Asp  Pro  Arg  His  Thr  Ser  Val  Tyr  Gly  Ser  Val  His  Ala  Ile
               420                 425                      430

GCT  GAT  GTG  GCT  TTT  TGC  ATG  GGC  TTT  GCT  ATA  GGC  TAT  TCT  GAG  TCA      2062
Ala  Asp  Val  Ala  Phe  Cys  Met  Gly  Phe  Ala  Ile  Gly  Tyr  Ser  Glu  Ser
          435                      440                      445

GGA  CTG  CCC  CAT  GGA  GAC  CCG  GAT  GTA  TCA  ACC  CAG  AAA  CCT  CTT  CCC      2110
Gly  Leu  Pro  His  Gly  Asp  Pro  Asp  Val  Ser  Thr  Gln  Lys  Pro  Leu  Pro
          450                      455                      460

TGG  ACC  AGT  CAC  CAT  GGC  TGACCCACGG  CTCAGTGGCC  TCAAAACCTC                     2158
Trp  Thr  Ser  His  His  Gly
465                      470

TGCCTGGGAT  CTTCTTCCTC  CCCTCCCATG  GAGACTGTCC  CTCATACTCT  TCTCACCTGT              2218

GTAACTTGTA  GCTCTTCMTC  TATGCCTTGG  TGCCGCAGTG  GCCCATCTTT  TATGGGAAGA              2278

CAGAGTGATG  CACCYYCCCG  CTGCTGTGAG  GTTGATTAAA  CTTGAGCTGT  GACGGGGTTC              2338

TGCAAGGGGT  GACTCATTGY  ATAGAGGTGG  TAGTGAGTAA  TGTGCCCCTG  AAACCAGTGG              2398

GGTGACTGAC  AAGCCTCTTT  AATCTGTTGC  CTGATTTTCT  CTGGCATAGC  CCCAACAGAT              2458

CGGAAGAGTG  TTACCCTCTT  TWCCCTCAAC  GTGTTCTTTC  CCGGGTTTTC  CCCAGCCGAG              2518

TTGAGAAAAT  GTTCTCAGCA  TTGTCTTGCT  GCCAAATGCC  AGCKTGAAGA  GTTWGGTATG              2578

KTTTTCTNC   CATTTATTTT  ATTTATTWAC  TAAAGTGAAT  GATTTTACTG  TGGYTAAATC              2638

TAGAGCTGCT  AAAAGGGCTT  TACCCTCAGT  GAAAAGTGTC  TTCTATTTNC  ATWATCTTTC              2698

AGAAACWGGA  GCCCATTTCT  CTTCTGGTGG  AGTTATNGAC  ATCCTCCTGA  CCNCCCCTGT              2758

GTNTCCTAC   CTNTACTGAA  CCTCTTAGAC  TCTNAGAAAT  AAAAGTAGAA  GAAAGACAGA              2818

AAAATTAACT  GATTAGACCC  AAGATTTCAT  GGGAAGAAGT  TAAAAGAAAC  TGCCTTGGAA              2878

ATCCCTC                                                                             2885
```

( 2 ) INFORMATION FOR SEQ ID NO:2:

( i ) SEQUENCE CHARACTERISTICS:
    ( A ) LENGTH: 470 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met  Leu  Arg  Pro  Ile  Leu  Asp  Ala  Pro  Gln  Arg  Leu  Leu  Lys  Glu  Gly
1                    5                   10                       15

Arg  Ala  Ser  Arg  Gln  Leu  Val  Leu  Val  Val  Phe  Val  Ala  Leu  Leu
               20                   25                       30

Leu  Asp  Asn  Met  Leu  Phe  Thr  Val  Val  Val  Pro  Ile  Val  Pro  Thr  Phe
               35                   40                       45

Leu  Tyr  Asp  Met  Glu  Phe  Lys  Glu  Val  Ile  Ser  Ser  Leu  His  Leu  Gly
          50                   55                   60

His  Ala  Gly  Ser  Ser  Pro  His  Ala  Leu  Ala  Ser  Pro  Ala  Phe  Ser  Thr
65                        70                   75                        80

Ile  Phe  Ser  Phe  Phe  Asn  Asn  Asn  Thr  Val  Ala  Val  Glu  Glu  Ser  Val
                    85                   90                       95

Pro  Ser  Gly  Ile  Ala  Trp  Met  Asn  Asp  Thr  Ala  Ser  Thr  Ile  Pro  Pro
               100                  105                      110

Pro  Ala  Thr  Glu  Ala  Ile  Ser  Ala  His  Lys  Asn  Asn  Cys  Leu  Gln  Gly
          115                  120                      125

Thr  Gly  Phe  Leu  Glu  Glu  Glu  Thr  Thr  Arg  Val  Gly  Val  Leu  Phe  Ala
     130                      135                      140
```

| Ser | Lys | Ala | Val | Met | Gln | Leu | Leu | Val | Asn | Pro | Phe | Val | Gly | Pro | Leu |
| 145 | | | | 150 | | | | | 155 | | | | | | 160 |

| Thr | Asn | Arg | Ile | Gly | Tyr | His | Ile | Pro | Met | Phe | Ala | Gly | Phe | Val | Ile |
| | | | | 165 | | | | | 170 | | | | | 175 | |

| Met | Phe | Leu | Ser | Thr | Val | Met | Phe | Ala | Phe | Ser | Gly | Thr | Tyr | Thr | Leu |
| | | | 180 | | | | | 185 | | | | | 190 | | |

| Leu | Phe | Val | Ala | Arg | Thr | Leu | Gln | Gly | Ile | Gly | Ser | Ser | Phe | Ser | Ser |
| | | 195 | | | | | 200 | | | | | 205 | | | |

| Val | Ala | Gly | Leu | Gly | Met | Leu | Ala | Ser | Val | Tyr | Thr | Asp | Asp | His | Glu |
| | 210 | | | | | 215 | | | | | 220 | | | | |

| Arg | Gly | Arg | Ala | Met | Gly | Thr | Ala | Leu | Gly | Gly | Leu | Ala | Leu | Gly | Leu |
| 225 | | | | | 230 | | | | | 235 | | | | | 240 |

| Leu | Val | Gly | Ala | Pro | Phe | Gly | Ser | Val | Met | Tyr | Glu | Phe | Val | Gly | Lys |
| | | | | 245 | | | | | 250 | | | | | 255 | |

| Ser | Ala | Pro | Phe | Leu | Ile | Leu | Ala | Phe | Leu | Ala | Leu | Leu | Asp | Gly | Ala |
| | | | 260 | | | | | 265 | | | | | 270 | | |

| Leu | Gln | Leu | Cys | Ile | Leu | Gln | Pro | Ser | Lys | Val | Ser | Pro | Glu | Ser | Ala |
| | | 275 | | | | | 280 | | | | | 285 | | | |

| Lys | Gly | Thr | Pro | Leu | Phe | Met | Leu | Leu | Lys | Asp | Pro | Tyr | Ile | Leu | Val |
| | 290 | | | | | 295 | | | | | 300 | | | | |

| Ala | Ala | Gly | Ser | Ile | Cys | Phe | Ala | Asn | Met | Gly | Val | Ala | Ile | Leu | Glu |
| 305 | | | | | 310 | | | | | 315 | | | | | 320 |

| Pro | Thr | Leu | Pro | Ile | Trp | Met | Met | Gln | Thr | Met | Cys | Ser | Pro | Lys | Trp |
| | | | | 325 | | | | | 330 | | | | | 335 | |

| Gln | Leu | Gly | Leu | Ala | Phe | Leu | Pro | Ala | Ser | Val | Ser | Tyr | Leu | Ile | Gly |
| | | | 340 | | | | | 345 | | | | | 350 | | |

| Thr | Asn | Leu | Phe | Gly | Val | Leu | Ala | Asn | Lys | Met | Gly | Arg | Trp | Leu | Cys |
| | | 355 | | | | | 360 | | | | | 365 | | | |

| Ser | Leu | Ile | Gly | Met | Leu | Val | Val | Gly | Thr | Ser | Leu | Leu | Cys | Val | Pro |
| | 370 | | | | | 375 | | | | | 380 | | | | |

| Leu | Ala | His | Lys | Asn | Phe | Gly | Leu | Ile | Gly | Pro | Asn | Ala | Gly | Leu | Gly |
| 385 | | | | | 390 | | | | | 395 | | | | | 400 |

| Leu | Xaa | Ile | Gly | Met | Val | Glu | Ser | Ser | Met | Pro | Ile | Met | Gly | His |
| | | | | 405 | | | | | 410 | | | | | 415 |

| Leu | Val | Asp | Pro | Arg | His | Thr | Ser | Val | Tyr | Gly | Ser | Val | His | Ala | Ile |
| | | | 420 | | | | | 425 | | | | | 430 | | |

| Ala | Asp | Val | Ala | Phe | Cys | Met | Gly | Phe | Ala | Ile | Gly | Tyr | Ser | Glu | Ser |
| | | 435 | | | | | 440 | | | | | 445 | | | |

| Gly | Leu | Pro | His | Gly | Asp | Pro | Asp | Val | Ser | Thr | Gln | Lys | Pro | Leu | Pro |
| | 450 | | | | | 455 | | | | | 460 | | | | |

| Trp | Thr | Ser | His | His | Gly |
| 465 | | | | | 470 |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GACTAAAGCT TAATGCTCCG GCCCATTCTG      30

( 2 ) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GAACTTCTAG ACGGTCAGCC ATGGTGACTG G                                31

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGGGATCCCT CCATGGCTCC GGCCCATTCT G                                31

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGGGATCCCG CTCAGCCATG GTGACTGGT                                   29

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GTCCAAGCTT GCCACCATGC TGCGGCCCAT TCTG                             34

(2) INFORMATION FOR SEQ ID NO:8:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CTAGCTCGAG TCAGCCATGG TGACTGGTAG CGTAGTCTGG GACGTCGTAT GGGTAGCA    58

(2) INFORMATION FOR SEQ ID NO:9:

(i) SEQUENCE CHARACTERISTICS:
        (A) LENGTH: 465 amino acids
        (B) TYPE: amino acid
        (C) STRANDEDNESS: Not Relevant (D) TOPOLOGY: linear (ii) MOLECULE TYPE: peptide (xi) SEQUENCE DESCRIPTION: SEQ ID NO:9:

| Met | Leu | Gln | Val | Val | Leu | Gly | Ala | Pro | Gln | Arg | Leu | Leu | Lys | Glu | Gly |
|---|---|---|---|---|---|---|---|---|---|---|---|---|---|---|---|
| 1 | | | | 5 | | | | | 10 | | | | | 15 | |

| Arg | Gln | Ser | Arg | Lys | Leu | Val | Leu | Val | Val | Phe | Val | Ala | Leu | Leu |
|---|---|---|---|---|---|---|---|---|---|---|---|---|---|---|
| | | | 20 | | | | 25 | | | | | 30 | | |

| Leu | Asp | Asn | Met | Leu | Leu | Thr | Val | Val | Val | Pro | Ile | Val | Pro | Thr | Phe |
|---|---|---|---|---|---|---|---|---|---|---|---|---|---|---|---|
| | | 35 | | | | | 40 | | | | | 45 | | | |

| Leu | Tyr | Ala | Thr | Glu | Phe | Lys | Asp | Ser | Asn | Ser | Ser | Leu | His | Arg | Gly |
|---|---|---|---|---|---|---|---|---|---|---|---|---|---|---|---|
| | | 50 | | | | 55 | | | | | 60 | | | | |

| Pro | Ser | Val | Ser | Ser | Gln | Gln | Ala | Leu | Thr | Ser | Pro | Ala | Phe | Ser | Thr |
|---|---|---|---|---|---|---|---|---|---|---|---|---|---|---|---|
| 65 | | | | | 70 | | | | 75 | | | | | | 80 |

| Ile | Phe | Ser | Phe | Phe | Asp | Asn | Thr | Thr | Thr | Thr | Val | Glu | Glu | His | Val |
|---|---|---|---|---|---|---|---|---|---|---|---|---|---|---|---|
| | | | | 85 | | | | | 90 | | | | | 95 | |

| Pro | Phe | Arg | Val | Thr | Trp | Thr | Asn | Gly | Thr | Ile | Pro | Pro | Pro | Val | Thr |
|---|---|---|---|---|---|---|---|---|---|---|---|---|---|---|---|
| | | | 100 | | | | | 105 | | | | | 110 | | |

| Glu | Ala | Ser | Ser | Val | Pro | Lys | Asn | Asn | Cys | Leu | Gln | Gly | Ile | Glu | Phe |
|---|---|---|---|---|---|---|---|---|---|---|---|---|---|---|---|
| | | | 115 | | | | | 120 | | | | | 125 | | |

| Leu | Glu | Glu | Glu | Asn | Val | Arg | Ile | Gly | Ile | Leu | Phe | Ala | Ser | Lys | Ala |
|---|---|---|---|---|---|---|---|---|---|---|---|---|---|---|---|
| | 130 | | | | | 135 | | | | | 140 | | | | |

| Leu | Met | Gln | Leu | Leu | Val | Asn | Pro | Phe | Val | Gly | Pro | Leu | Thr | Asn | Arg |
|---|---|---|---|---|---|---|---|---|---|---|---|---|---|---|---|
| 145 | | | | | 150 | | | | | 155 | | | | | 160 |

| Ile | Gly | Tyr | His | Ile | Pro | Met | Phe | Val | Gly | Phe | Met | Ile | Met | Phe | Leu |
|---|---|---|---|---|---|---|---|---|---|---|---|---|---|---|---|
| | | | | 165 | | | | | 170 | | | | | 175 | |

| Ser | Thr | Leu | Met | Phe | Ala | Phe | Ser | Gly | Thr | Tyr | Ala | Leu | Leu | Phe | Val |
|---|---|---|---|---|---|---|---|---|---|---|---|---|---|---|---|
| | | | 180 | | | | | 185 | | | | | 190 | | |

| Ala | Arg | Thr | Leu | Gln | Gly | Ile | Gly | Ser | Ser | Phe | Ser | Ser | Val | Ala | Gly |
|---|---|---|---|---|---|---|---|---|---|---|---|---|---|---|---|
| | | 195 | | | | | 200 | | | | | 205 | | | |

| Leu | Gly | Met | Leu | Ala | Ser | Val | Tyr | Thr | Asp | Asn | Tyr | Glu | Arg | Gly | Arg |
|---|---|---|---|---|---|---|---|---|---|---|---|---|---|---|---|
| | 210 | | | | | 215 | | | | | 220 | | | | |

| Ala | Met | Gly | Ile | Ala | Leu | Gly | Gly | Leu | Ala | Leu | Gly | Leu | Leu | Val | Gly |
|---|---|---|---|---|---|---|---|---|---|---|---|---|---|---|---|
| 225 | | | | | 230 | | | | | 235 | | | | | 240 |

| Ala | Pro | Phe | Gly | Ser | Val | Met | Tyr | Glu | Phe | Val | Gly | Lys | Ser | Ser | Pro |
|---|---|---|---|---|---|---|---|---|---|---|---|---|---|---|---|
| | | | | 245 | | | | | 250 | | | | | 255 | |

| Phe | Leu | Ile | Leu | Ala | Phe | Leu | Ala | Leu | Leu | Asp | Gly | Ala | Leu | Gln | Leu |
|---|---|---|---|---|---|---|---|---|---|---|---|---|---|---|---|
| | | | 260 | | | | | 265 | | | | | 270 | | |

| Cys | Ile | Leu | Trp | Pro | Ser | Lys | Val | Ser | Pro | Glu | Ser | Ala | Met | Gly | Thr |
|---|---|---|---|---|---|---|---|---|---|---|---|---|---|---|---|
| | | 275 | | | | | 280 | | | | | 285 | | | |

| Ser | Leu | Leu | Thr | Leu | Leu | Lys | Asp | Pro | Tyr | Ile | Leu | Val | Ala | Ala | Gly |
|---|---|---|---|---|---|---|---|---|---|---|---|---|---|---|---|
| | 290 | | | | | 295 | | | | | 300 | | | | |

| Ser | Ile | Cys | Leu | Ala | Asn | Met | Gly | Val | Ala | Ile | Leu | Glu | Pro | Thr | Leu |
|---|---|---|---|---|---|---|---|---|---|---|---|---|---|---|---|
| 305 | | | | | 310 | | | | | 315 | | | | | 320 |

| Pro | Ile | Trp | Met | Met | Gln | Thr | Met | Cys | Ser | Pro | Glu | Trp | Gln | Leu | Gly |
|---|---|---|---|---|---|---|---|---|---|---|---|---|---|---|---|
| | | | | 325 | | | | | 330 | | | | | 335 | |

| Leu | Ala | Phe | Leu | Pro | Ala | Ser | Val | Ala | Tyr | Leu | Ile | Gly | Thr | Asn | Leu |
|---|---|---|---|---|---|---|---|---|---|---|---|---|---|---|---|
| | | | 340 | | | | | 345 | | | | | 350 | | |

| Phe | Gly | Val | Leu | Ala | Asn | Lys | Met | Gly | Arg | Trp | Leu | Cys | Ser | Leu | Val |
|---|---|---|---|---|---|---|---|---|---|---|---|---|---|---|---|
| | | 355 | | | | | 360 | | | | | 365 | | | |

| Gly | Met | Val | Ala | Val | Gly | Ile | Ser | Leu | Leu | Cys | Val | Pro | Leu | Ala | His |
|---|---|---|---|---|---|---|---|---|---|---|---|---|---|---|---|
| | 370 | | | | | 375 | | | | | 380 | | | | |

| Asn | Ile | Phe | Gly | Leu | Ile | Gly | Pro | Asn | Ala | Gly | Leu | Gly | Phe | Ala | Ile |
|---|---|---|---|---|---|---|---|---|---|---|---|---|---|---|---|
| 385 | | | | | 390 | | | | | 395 | | | | | 400 |

| | | | | | | | | | | | | | | |
|---|---|---|---|---|---|---|---|---|---|---|---|---|---|---|
| Gly | Met | Val | Asp | Ser<br>405 | Ser | Leu | Met | Pro | Ile<br>410 | Met | Gly | Tyr | Leu | Val<br>415 | Asp |
| Leu | Arg | His | Thr<br>420 | Ser | Val | Tyr | Gly | Ser<br>425 | Val | Tyr | Ala | Ile | Ala<br>430 | Asp | Val |
| Ala | Phe | Cys<br>435 | Val | Gly | Phe | Ala | Ile<br>440 | Gly | Pro | Ser | Thr | Gly<br>445 | Gly | Val | Ile |
| Val | Gln<br>450 | Val | Ile | Gly | Phe | Pro<br>455 | Trp | Leu | Met | Val | Ile<br>460 | Ile | Gly | Thr | Ile |
| Asn<br>465 | | | | | | | | | | | | | | | |

What is claimed is:

1. An isolated polypeptide having an amino acid sequence selected from the group consisting of:
   (a) amino acids 1 to 470 of SEQ ID NO:2;
   (b) amino acids 2 to 470 of SEQ ID NO:2; and
   (c) the amino acid sequence of the human amine transporter polypeptide having the amino acid sequence encoded by the cDNA clone contained in ATCC Deposit No. 75980.

2. The isolated polypeptide of claim 1, wherein said polypeptide has the amino acid sequence of amino acids 1 to 470 of SEQ ID NO:2.

3. The isolated polypeptide of claim 1, wherein said polypeptide has the amino acid sequence of amino acids 2 to 470 of SEQ ID NO:2.

4. The isolated polypeptide of claim 1, wherein said polypeptide has the amino acid sequence as encoded by the cDNA clone contained in ATCC Deposit No. 75980.

5. The isolated polypeptide of claim 1, which is produced or contained in a recombinant host cell.

6. The isolated polypeptide of claim 5, wherein said recombinant host cell is mammalian.

7. An isolated polypeptide encoded by a polynucleotide that hybridizes under stringent conditions with a polynucleotide of SEQ ID NO: 1 or the complement thereof, wherein said polypeptide retains substantially the same activity as a polypeptide having the amino acid sequence of amino acids 1 to 470 or 2 to 470 of SEQ ID NO:2.

8. An isolated polypeptide wherein, except for one or more conservative amino acid substitutions, said polypeptide has a sequence selected from the group consisting of:
   (a) amino acids 1 to 470 of SEQ ID NO:2; and
   (b) amino acids 2 to 470 of SEQ ID NO:2, wherein said polypeptide retains substantially the same activity as a polypeptide having the amino acid sequence of amino acids 1 to 470 or 2 to 470 of SEQ ID NO:2.

* * * * *

UNITED STATES PATENT AND TRADEMARK OFFICE
CERTIFICATE OF CORRECTION

PATENT NO. : 5,859,200

DATED : January 12, 1999

INVENTORS : Li *et al.*

It is certified that an error appears in the above-identified patent and that said Letters Patent is hereby corrected as shown below.

In column 31, Claim 1, after "isolated polypeptide", please delete "having" and insert therein --comprising--.

In column 32, Claim 8, after "said polypeptide", please delete "has" and insert therein --comprises--.

Signed and Sealed this

Twelfth Day of October, 1999

Attest:

Q. TODD DICKINSON

*Attesting Officer*  *Acting Commissioner of Patents and Trademarks*